United States Patent [19]

Cavazza

[11] 4,021,436
[45] May 3, 1977

[54] DERIVATIVES OF NICOTINIC ACID WITH AMINES VARIOUSLY SUBSTITUTED

[76] Inventor: Claudio Cavazza, Via Marocco, 35, Rome, Italy

[22] Filed: Feb. 2, 1976

[21] Appl. No.: 654,223

Related U.S. Application Data

[63] Continuation-in-part of Ser. No. 451,695, March 15, 1974, abandoned.

[52] U.S. Cl. ............... 260/294.8 E; 260/295.5 A; 424/266
[51] Int. Cl.² ........................................ C07D 213/56
[58] Field of Search ............ 260/294.8 E, 295.5 A, 260/295 AM; 424/266

[56] References Cited

UNITED STATES PATENTS 2,493,645  1/1950  Schlapfer .................... 260/295.5 A
3,155,672  11/1964  Pasini et al. ................. 260/295 AM Primary Examiner—Alan L. Rotman
Attorney, Agent, or Firm—Robert E. Burns; Emmanuel J. Lobato; Bruce L. Adams

[57] ABSTRACT

A novel thionicotinate of nicotinamide is disclosed having the formula:

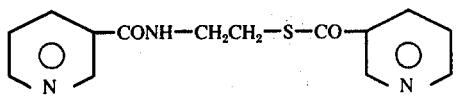

The compound has the useful pharmacological activity of lowering cholesterol, free fatty acid and triglyceride plasma levels. In cases of liver injury, administration of the compound has modified toward normal the injury-induced malfunction of the liver. A synthesis of the compound from nicotinoyl chloride hydrochloride is described as well as modes for the administration of the compound.

1 Claim, 3 Drawing Figures

EFFECT OF $ST_9$, 117 MG/KG OS, ON LIPID MOBILIZATION IN 17-H FASTED RATS. PLASMA AVERAGE VALUES ± S.E.M. IN PER CENT OF VALUES IN CONTROLS (F.F.A. 1001± 82.45 µEq/L, TRIGLYCERIDES 40.93± 3.14 MC/100 ML) AT DIFFERENT TIMES AFTER ADMINISTRATION. F.F.A. (——) TRIGLYCERIDES (----). □ , △ , AND ▲ INDICATE NON SIGNIFICANT DIFFERENCE, P=.01, AND P=.001, SIGNIFICANT DIFFERENCE RESPECTIVELY. N= 10 PER GROUP.

$ST_9$ = NICOTINAMIDE -N-ETHYL-THIONICOTINATE

PLASMA BSP CLEARANCE IN RATS TREATED WITH $ST_9$, 117 MG/KG (——) AND 233 MG/KG (----) OS 1-H BEFORE, 7 AND 23-H AFTER $CCL_4$. N=10 PER GROUP. BSP WAS GIVEN 3-H AFTER LAST DOSE OF $ST_9$. AVERAGE VALUES ±S.E.M. STUDENT'S "t" TEST VERSUS CONTROLS. □ , △ AND ▲ INDICATE NON SIGNIFICANT DIFFERENCE, P=.01 AND P=.001, SIGNIFICANT DIFFERENCE RESPECTIVELY.

$ST_9$ = NICOTINAMIDE -N-ETHYL-THIONICOTINATE

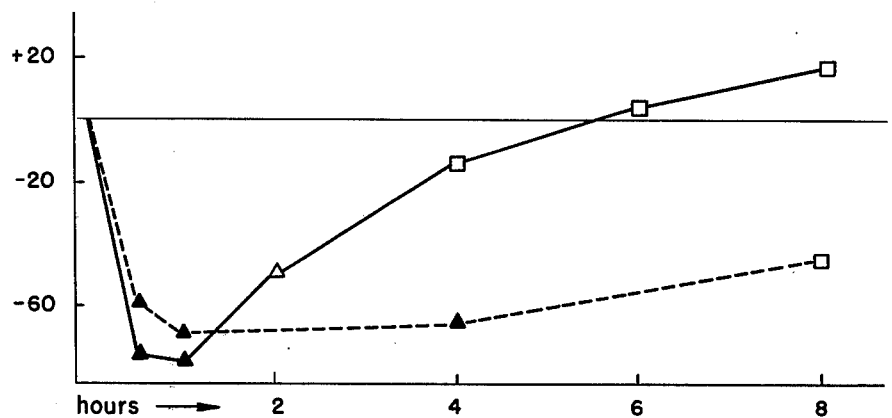

EFFECT OF ST$_9$, 117 MG/KG OS, ON LIPID MOBILIZATION IN 17-H FASTED RATS. PLASMA AVERAGE VALUES ± S.E.M. IN PER CENT OF VALUES IN CONTROLS (F.F.A. 1001 ± 82.45 µEq/L, TRIGLYCERIDES 40.93 ± 3.14 MC/100 ML) AT DIFFERENT TIMES AFTER ADMINISTRATION. F.F.A. (——) TRIGLYCERIDES (----). □, △, AND ▲ INDICATE NON SIGNIFICANT DIFFERENCE, P=.01, AND P=.001, SIGNIFICANT DIFFERENCE RESPECTIVELY. N= 10 PER GROUP.

ST$_9$ = NICOTINAMIDE - N - ETHYL - THIONICOTINATE

*FIG. 1*

EFFECT OF ST$_9$ ON NOR-ADRENALINE □——□ (0.15 MCG/ML) AND 3'5' AMPc O-----O (174.6 MCG/ML) IN AN ISOLATED FAT CELL SYSTEM FROM RAT EPIDIDYMAL ADIPOSE TISSUE. RATE ± E.S.M. OF NOR-ADRENALINE INDUCED LIPOLYSIS WAS 5.38 ± 0.28 µEq/gr/HOUR OF TISSUE. RATE ± E.S.M. OF 3'5' AMPc INDUCED LIPOLYSIS WAS 35 ± 3 µEq/gr/3 HOURS

ST$_9$ = NICOTINAMIDE-N-ETHYL-THIONICOTINATE

PLASMA BSP CLEARANCE IN RATS TREATED WITH $ST_9$, 117 MG/KG (—·—·) AND 233 MG/KG (-----) OS 1-H BEFORE, 7 AND 23-H AFTER $CCL_4$. N = 10 PER GROUP. BSP WAS GIVEN 3-H AFTER LAST DOSE OF $ST_9$. AVERAGE VALUES ± S.E.M. STUDENT'S "t" TEST VERSUS CONTROLS. □ , △ AND ▲ INDICATE NON SIGNIFICANT DIFFERENCE, P=.01 AND P=.001, SIGNIFICANT DIFFERENCE RESPECTIVELY.

$ST_9$ = NICOTINAMIDE-N-ETHYL-THIONICOTINATE

DERIVATIVES OF NICOTINIC ACID WITH AMINES VARIOUSLY SUBSTITUTED

RELATED APPLICATIONS

This application is a Continuation-in-Part of patent application S.N. 451,695 filed March 15, 1974 and herewith abandoned.

FIELD OF THE INVENTION

This invention relates to the novel nicotinic acid amide Nicotinamide-N-ethyl-thionicotinate and more particularly to its synthesis, utility and modes for its useful administration.

THE INVENTION

The compound Nicotinamide-N-ethyl-thionicotinate having the formula:

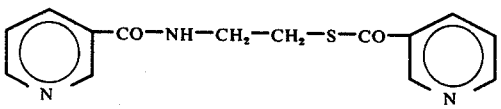

and its pharmaceutically acceptable salts have useful pharmacological activity related to liver function and indicated therapeutic activity in liver malfunction.

DETAILED DESCRIPTION OF THE INVENTION

The invention above will be more fully described by the appended examples and by references to the drawing where:

FIG. 1 shows the effect of the compound of the invention on lipid metabolism (FFA and triglycerides) in fasted rats.

Figure 2:
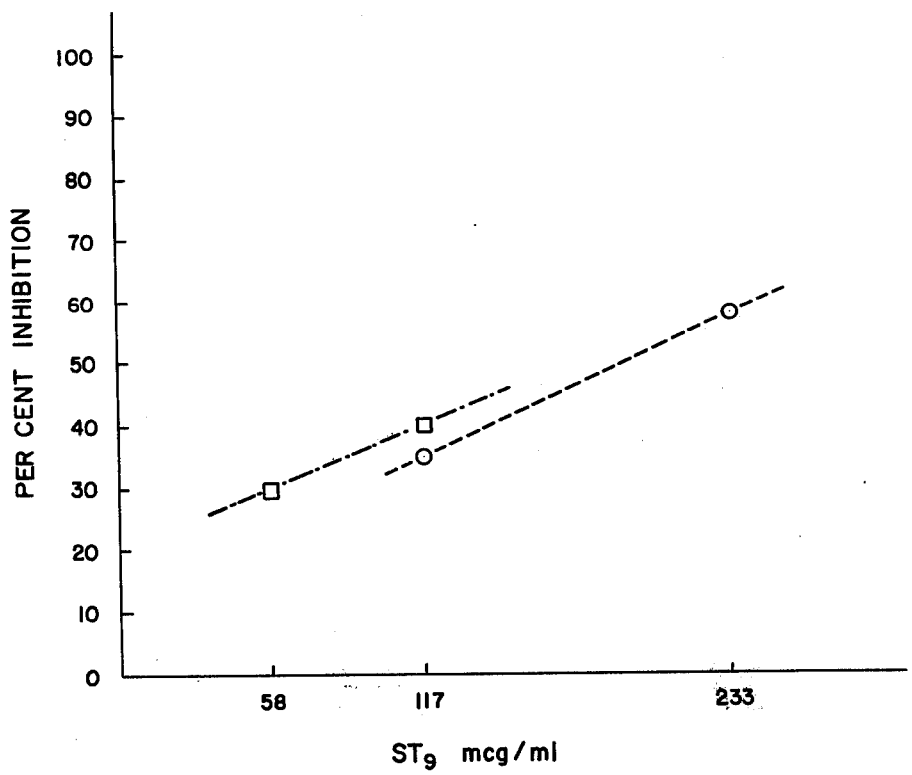
FIG. 2 shows the effect of the compound of the invention on nor-adrenaline and 3'5-AMPc-treated adipose tissue.

The compound is prepared by reacting nicotinyl chloride hydrochloride or nicotinic acid esters with cysteamine in the presence of triethylamine or other strong proton or halogen acid acceptors.

Preferably the reaction is carried out in anhydrous organic solvents such as chloroform, methyl alcohol ethyl alcohol, dioxane, tetrahydrofurane, (THF), N,N-dimethyl formamide (DMF). Part of the solvent medium may be the anhydrous proton or haloacid acceptor. Among such anhydrous acceptors are triethylamine, other trialkylamines, pyridine etc.

The reaction of the nicotinic acid.HCl or ester with the cysteamine proceeds at temperatures between 25° and 90° C. Preferably the reaction provides purer products in best yield at temperatures in the range 60°– 70° C.

The nicotinamide-N-ethyl-nicoinate may be prepared into nontoxic pharmaceutically acceptable salts with organic acids such as acetic, citric, tartaric, salicylic, maleic etc. or with inorganic acid such as hydrochloric and hydrobromic acid, sulfuric acid, nitric acid, phosphoric acid and the haloacids.

This compound has been found to be active pharmacologically by reducing cholesterol, free-fatty acid and triglyceride levels in plasma after administration. Such pharmacological activity is associated with the function of the liver and the compound has been noted to counteract abnormalities resulting from experimentally-induced liver malfunction, thus indicating therapeutic activity.

The exact mode or situ of such activity in the organism is as yet unclear but the activity is unmistakable. An additional factor of utility of the compounds for therapy as compared to related nicotinic acid derivatives is its low toxicity, high therapeutic index and the absence of hypotensive effects previously noted for nicotinic acid.

The appended examples indicate a useful simple and preferred synthesis of the novel compound, its pharmacological activity and its therapeutic activity. The synthetic methods and the modes of administration are merely exemplary. All art-recognized equivalent methods and materials are intended.

EXAMPLE 1

Nicotinamide-N-ethyl-thionicotine

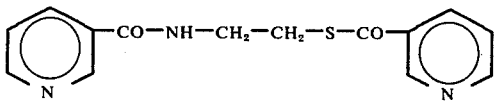

Load a flask, provided with reflux condenser with 20 gm of nicotinic acid and 40 cc of thionyl chloride. Reflux the mixture for 8 hours. At the end of the reaction, the excess thionyl chloride is distilled. Wash the residue-nicotinyl chloride hydrochloride several times with anhydrous benzol. Filter and dry. Suspend 0.6 moles of the nicotinoyl chloride hydrochloride in 350 cc of anhydrous chloroform.

Add 1.2 moles of anhydrous triethylamine and 0.35 moles of cysteamine previously dissolved in 150 ml of anhydrous chloroform. Keep the mixture stirring for 7 hours at 60°–70° C.

The organic solution is extracted 3 times with water (350 cc). Evaporate the organic layer to dryness in vacuo. Dissolve the obtained solid compound with hot methyl alcohol and add 20 g of active charcoal. After filtration, a white crystalline solid substance is obtained (melting point: 148°–150° C.).

EXAMPLE 2

-Toxicity-

The compound of Example 1 (ST-9) has an $LD_{50}$ of 2500 mgm/kg per os in rats.

EXAMPLE 3

-Pharmacological Activity-

The pharmacological activity of the compound ST-9 was assessed by using the methods described in the following articles:

The antilipolytic activity in the fasting state was studied in accordance with

1. Carlson L. A. and E. R. Nye, Acute effect of Nicotinic acid in the rat. Plasma and liver lipids and blood glucose. Acta Med. Scand., 179, 453, 1966.

2. Dalton C., C. Van Trabert and J. X. Dwyer, Relationship of Nicotinamide and Nicotinic acid to Hypolipidemia, Biochemical Phrmacology, 19, 2609, 1970.

3. Bizzi A. and S. Garattini Drugs lowering plasma free fatty acids: similarities and dissimilarities with Nicotinic acid effect, p. 207. K. F. Gey and L. A. Carlson Edrs. Hans Huber Publisher, Bern Stuttgard Vienna, 1971.

The hypocholesterolaemic action was studied in accordance with

1. Ranney R. E., Cook D. L., Hambourger W. E., J. Pharmacol. Expl. Therap., 142, 132, 1963.

The antilipolytic activity in the case of Nor-Adrenaline stimulated lipolysis in rats was investigated in accordance with 1. S. Garattini and A. Bizzi Inhibiteurs de la mobilization des acides gras libres, Actualite Pharmacologiques XXII Serie, 169, 1969 and the results were as follows:

117 mg/kg os lowered the plasma levels of free fatty acids (FFA) by 80% and triglycerides by 70% in 17-h fasted rats (FIG. 1).

233 mg/kg os reduced the lipolytic activity of subcutaneously injected Nor-adrenaline by 90% in rats.

Hypocholesterolaemic action: 117 mcg/kg/ daily for 12 days lowered the plasma levels of cholesterol in rats.

The antilipolytic activity "in vitro" was studied in accordance with

Monsinger B., M. Vanghan, Advances in Experimental medicine and Biology Drugs affecting Lipid Metabolism, Vol. 4, pg. 63 Edrs Holmes, Carlson, Paoletti Plenum Press New York 1969.

The "in vitro" results were as follows:

58 mcg/ml reduced the "in vitro" lipolytic activity of 0.15 mcg/ml Nor-adrenaline on rat epididymal adipose tissue by 40 percent (FIG. 2), 200 mcg/ml inhibited by 58 percent the "in vitro" F.F.A. release due to cyclic adenilate (FIG. 2).

EXAMPLE 4
-Therapeutic Indictions-

Figure 3:
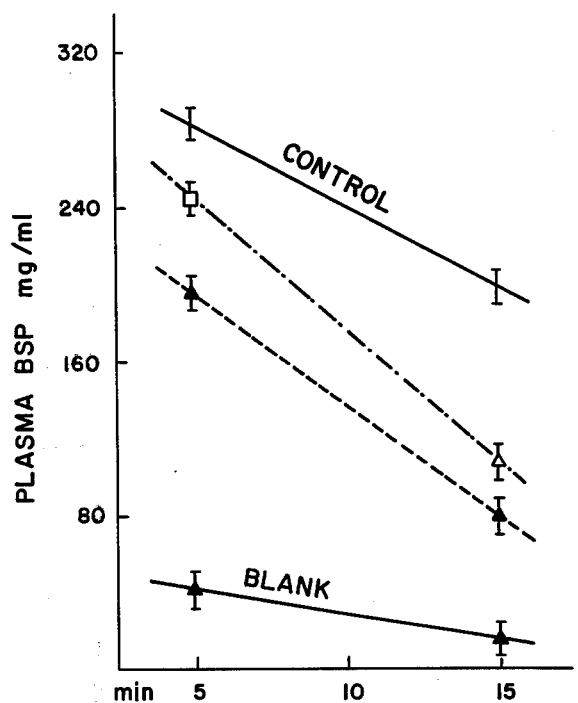
FIG. 3 shows the plasma BSP clearance in $CCl_4$ toxic and nontoxic rats comparing treated and untreated controls.

The activity of ST-9 in experimental liver injury was studied according to the methods of 1. Schwarzmann W., Les hepatites toxiques experimentales, Revue Int. d'Hepatol., 5, 387, 1957. and
2. Stern P. H., T. Fuzukawa, T. M. Brody, Rat liver and plasma lipids after CCl administration J. Lipid Res., 6, 278, 1965. The action in experimental liver injury of ST-9 was as follows: doses of 233 mcg/kg per os and 117 mcg/kg/per os per reduced the changes in the plasma and hepatobiochemical pattern (plasma GPT, GOT, LDH, total lipids, triglycerides, cholesterol and $\beta$-lipoproteins, and liver total lipids, triglycerides, cholesterol and glycogen) induced by carbon-tetrachloride and by d-1 aetionine in rats and increased plasma clearance of Bromosulphonphthalein (FIG. 3).

EXAMPLE 5

The various experimental animals used in the above tests were carefully observed and no untoward or unusual toxic syndromes were noted in other than the $LD_{50}$ test. It was noted however, in a parallel comparison study, concurrently run, that ST-9 did not show any hypotensive effect comparable to that of nicotinic acid.

Thus Nicotinamide-N-ethyl-thio-nicotinate is capable of reducing hyperlipidaemic levels under conditions of stimulated lipid mobilization and under experimentally simulated and induced conditions of altered lipid metabolism.

The invention includes within its scope pharmaceutical preparations containing, as an active ingredient, the therapeutically active compound nicotinamide-N-ethyl thionicotinate or the non-toxic acid addition salt thereof, in association with a pharmacologically acceptable carrier. Other therapeutic and compatible materials may be included in the preparation. The preparations may take any of the forms customarily employed for administration of therapeutically active substances, but the preferred types are those suitable for oral administration and especially tablets, pills and capsules including the substance. The tablets and pills may be formulated in the usual manner with one or more pharmacologically acceptable diluents or excipients, for example lactose or starch, and include materials of a lubricating nature, for example calcium stearate. Capsules made of absorbable material, such as gelatin, may contain the active substance alone or in admixture with a solid or liquid diluent. Liquid preparations may be in the form of suspensions, emulsions, syrups or elixirs of the active substance in water or other liquid media commonly used for making orally acceptable pharmaceutical formulations, such as liquid paraffin, or a syrup or elixir base. The active substance may also be provided when indicated, in a form suitable for parenteral administration, i.e. as a suspension or emulsion in sterile water or an organic liquid usually employed for injectable preparations, for example a vegetable oil such as olive oil, or a sterile solution in an organic solvent.

The following Examples illustrate the preparation of a pharmaceutical composition according to the invention.

EXAMPLE 25 g of Nicotinamide N-ethyl Nicotinate, 25 g of Avicel PH 101 (microcrystalline cellulose) and 1 g of Aerosil (highly purified silicon dioxide) are mixed together and gelatin capsules are filled each with the mixture so that each capsule contains 10 mg of active substance.

EXAMPLE 800 g of lactose and 200 g of maize starch are mixed with 200 ml of 5% maize starch in water. The mixture is granulated, dried at 55° C and sieved through a no. IV sieve (Sieve opening 0.7 mm). 1000 g of the granulate are mixed with 100 g of Nicotinamide N-ethyl Nicotinate and gelatin capsules are filled each with the mixture so that each capsule contains 10 mg of active substance.

What is claimed:

1. The compound Nicotinamide-N-ethyl-thionicotinate and the non-toxic acid addition salts thereof.

* * * * *